United States Patent [19]

Rothgery et al.

[11] Patent Number: 4,871,861

[45] Date of Patent: Oct. 3, 1989

[54] SUBSTITUTED 5-AMIDOTETRAZOLES

[75] Inventors: Eugene F. Rothgery, North Branford; Steven A. Manke, Wallingford, both of Conn.

[73] Assignee: Olin Corporation, Cheshire, Conn.

[21] Appl. No.: 70,454

[22] Filed: Jul. 6, 1987

[51] Int. Cl.$^4$ .............................................. C07D 257/06
[52] U.S. Cl. ....................................... 548/251; 521/90
[58] Field of Search ............................ 521/90; 548/251

[56] References Cited

U.S. PATENT DOCUMENTS

| | | | |
|---|---|---|---|
| 3,338,915 | 8/1967 | Brown | 260/299 |
| 3,366,581 | 1/1968 | Reed | 260/2.5 |
| 3,374,188 | 3/1968 | Marsh et al. | 260/2.5 |
| 3,442,829 | 5/1969 | Moore et al. | 260/2.5 |
| 3,873,477 | 3/1975 | Beck et al. | 260/2.5 |
| 4,126,590 | 11/1978 | Illy | 200/2.5 N |

FOREIGN PATENT DOCUMENTS 0914584  3/1982  U.S.S.R. ............................... 521/90
1598900  9/1981  United Kingdom .

OTHER PUBLICATIONS

Olin Product Data Sheet "EXPANDEX ® 5PT High Temperature Blowing Agent", Olin Corporation, 1983.

Primary Examiner—David B. Springer
Attorney, Agent, or Firm—James B. Haglind

[57] ABSTRACT

In a process for the production of cellular products comprising thermoplastic or rubber materials the blowing agents employed have the formula:

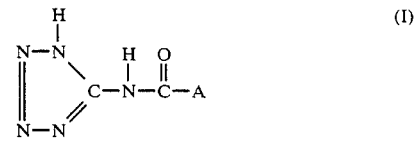

wherein
A represents NHX, NRR' or OR
X represents H or a lower alkyl group,
R represents a lower alkyl group, and
R' represents a lower alkyl group.

The novel blowing agents provide high gas yields and have high decomposition temperatures while forming only inert nitrogen gas. They are particularly suitable for the production of cellular products from high temperature thermoplastic materials such as polycarbonates.

4 Claims, No Drawings

SUBSTITUTED 5-AMIDOTETRAZOLES

This invention is related to blowing agents for cellular or plastic foams. More particularly, the invention is related to selected tetrazole compounds used as blowing agents in the production of foamed plastics.

The use of blowing agents in the manufacture of cellular or foamed synthetic plastic products is well established. A blowing agent is a chemical compound which decomposes on heating to a specific temperature, to yield a vapor or gas or mixture of vapors and gases. In use, the blowing agent is incorporated in the thermoplastic material at a temperature below the decomposition temperature of the blowing agent and the mixture subsequently heated to a temperature above the decomposition temperature of the blowing agent whereupon the blowing agent decomposes to liberate a gas or vapor which forms small voids within the thermoplastic material. It is, of course, of importance that the blowing agent be finely and homogeneously dispersed within the thermoplastic material.

An important characteristic of a blowing agent is the temperature at which it decomposes to liberate gas or vapor since this temperature limits the temperature at which other operations may be performed on the thermoplastic material after incorporation of the blowing agent but before actual formation of the cellular product. It is, therefore, often of convenience to employ a blowing agent having a relatively high temperature of decomposition, this being especially the case when forming cellular products of thermoplastic material having relatively high fusion temperatures.

Tetrazole compounds have been previously employed as blowing agents for plastic materials. For example, 5-cyanovinyltetrazoles are described as being suitable for blowing agents in U.S. Pat. No. 3,338,915, issued Aug. 29, 1967 to M. Brown.

U.S. Pat. No. 3,366,581, issued Jan. 30, 1968 to R. A. Reed et al teaches the use of 5-hydroxytetrazole as a high temperature blowing agent for thermoplastic resins including polyolefins, polyamides, acrylonitrile-butadiene-styrene resins, and high temperature silicone rubbers.

The ammonium salt of 5-azidotetrazole is useful as a blowing agent for producing any of the polymeric materials conventionally used in forming cellular products according to U.S. Pat. No. 3,374,188, issued Mar. 19, 1968 to F. D. Marsh et al.

Aliphatic or aromatic substituents on the 5-position of the tetrazole rings are taught in U.S. Pat. No. 3,442,829, issued May 6, 1969 to L. D. Moore et al as suitable blowing agents for a wide variety of rubbers and thermoplastic materials. Commercially 5-phenyltetrazole has been employed extensively in producing cellular thermoplastic materials.

In addition, tetrazole metallic salts of Zn, Ba, Ca, Pb, and Al have been described as suitable blowing agents for polymers such as polycarbonates and polysulfone in U.S. Pat. No. 3,873,477, issued Mar. 25, 1975 to W. Beck et al; as well as the 5-sulfonylalkylene substituted tetrazoles taught in U.S. Pat. No. 4,126,590 issued Nov. 21, 1978 to H. Illy.

Now it has been found that selected substituted 5-amidotetrazoles are highly effective blowing agents for use at high temperatures in the production of cellular thermoplastic materials from resins such as polycarbonates. The novel blowing agents of the present invention are compounds of the formula:

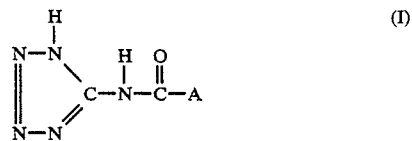

wherein
A represents NXH, NRR' OR
X represents H or a lower alkyl group,
R represents a lower alkyl group, and
R' represents a lower alkyl group.

More in detail, the novel blowing agents of the present invention are substituted 5-amido tetrazoles having thermal decomposition temperatures above about 250° C. which provide copious amounts of gas without the formation of ammonia as an undesired contaminant.

Novel blowing agents of formula I include 5-amidotetrazole compounds in which A represents NHX where X can be H or a lower alkyl group. In these compounds which are also known as N'-alkyl-N-(tetrazol-5-yl) ureas, the lower alkyl groups have from 1 to about 6 carbon atoms. Suitable as blowing agents are 5-amidotetrazole compounds in which A is, for example, an amino, methylamino, ethylamino, propylamino, isopropylamino, butylamino, isobutylamino, sec-butylamino, tertbutylamino, pentylamino, neopentylamino, or hexylamino group.

N'-alkyl-N-(tetrazol-5-yl) ureas can be prepared by any suitable method including the reaction of 5-aminotetrazole with an alkylisocyanate. The reaction preferably employs a solvent such as dimethylformamide or acetonitrile.

Novel compounds which are employed as blowing agents for thermoplastic materials are those of formula I in which A represents NRR' where R and R' are individually selected alkyl radicals. Suitably represented by R and R' are alkyl radicals having from 1 to about 6 carbon atoms. The novel compounds include those in which A represents, for example, a dimethylamino, ethylmethylamino, diethylamino, diisopropylamino, ethylbutylamino, dibutylamino, disec-butylamino, ditertbutylamino, dipentylamino, dineopentylamino, hexylmethylamino, or dihexylamino group.

The novel dialkyl amino derivatives are prepared by the reaction of 5-aminotetrazole with a dialkylcarbamoyl halide. The reaction is preferably carried out under reflux in a solvent such as dimethylformamide or acetonitrile and the like. In addition, the reaction mixture may include a halogen acid scavenger, for example, a trialkylamine or an inorganic base such as an alkali metal hydroxide or carbonate compound.

Blowing agents of formula 1 in which A represents the group OR are tetrazol-5-yl carbamic acid esters in which R is a lower alkyl radical having from 1 to about 6 carbon atoms. Suitable ester groups include those in which R is a methyl, ethyl, propyl, isopropyl, butyl, or secbutyl tertbutyl, pentyl, neopentyl or hexyl radical.

The novel blowing agents of the present invention are used in the production of cellular products of thermoplastic or rubber materials which allow processing at elevated temperatures. For example, they may be used with polyolefins; acrylonitrile-butadiene-styrene resins; polyvinyl halides; polyacrylates; polyamides, polyetherimides; polycarbonates; polyphenylene oxides; polybutylene terphthalate; polyphenylene sulfides; polysulfones; polysulfonates; rubbers including silicone rubbers, polybutadiene and polyisoprene, and the like, as well as copolymers and graft polymers. The blowing agents of this invention are especially useful, as indicated, with polymers and copolymers that have high processing temperatures such as polycarbonates, polyphenylene sulfides and polybutylene phthalate.

The substituted 5-amidotetrazole blowing agents may be employed by incorporating a small, but effective, blowing amount of the material into a gas-expandable polymer. The amount of such material will vary, depending on the polymer foam density desired and other processing and temperature factors which are well known. However, typically, the compounds may be employed by incorporating, for example, from about 0.10 to about 15 percent by weight of the compound as a blowing agent; preferably, from about 0.15 to 5.0 percent, in preparing rigid or structural foam products such as those of polycarbonate resins. The blowing agents may be employed in various particle sizes, and alone or in combination with other blowing agents, stabilizers, antioxidants, fillers, plasticizers, cross-linking agents, dyes, pigments, carbon and other additives employed in polymeric compositions.

The novel blowing agents of the present invention may be admixed, for example, with a polycarbonate homopolymer in a Banbury mixer, and the mixed mass milled into a large sheet or other form and subsequently processed into pellets. The polycarbonate homopolymer containing the blowing agent may then be placed or extruded into a multicavity mold and preheated to a temperature above the blowing temperature of the blowing agent for a period of time to produce a rigid structural foam polycarbonate product. Since only inert gases such as nitrogen gas are produced in the process, no detrimental effects on the polycarbonate foam product result.

High temperature processing polymer foam products are also prepared by casting, molding or injection molding, such as, for example, by preparing the products by heating the gas-expandable polymer during the injection-molding of the polymer with an injection machine at a temperature above the compounding temperature of the product.

To further illustrate the present invention, the following examples are given with no intention of being limited thereby. All parts and percentages are by weight unless otherwise stated.

EXAMPLE 1

N-(Tetrazol-5-yl) urea

5-Aminotetrazole hydrate (10.3 g, 0.1 mole) was slurried into 150 ml of water containing 10 ml of 37 percent HCl. A solution of potassium cyanate (10 g, 0.12 mole) was added at ambient temperature over the course of one hour. When a slight exotherm began, the solution was cooled to 10° C. The mixture was stirred two hours, filtered and recrystallized from ethanol.

Melting point: >305° C.

Elemental analysis Calc.: C, 18.76; H, 3.15; N, 65.61. Found: C, 18.72; H, 3.35; N, 65.85.

EXAMPLE 2

N',N'-Dimethyl-N-(tetrazol-5-yl) urea

Anhydrous 5-aminotetrazole (8.5 g, 0.1 mole) was slurried in 150 ml of acetonitrile. On the addition of triethylamine (10 g, 0.1 mole), the solids dissolved. Dimethylcarbamoyl chloride (13 g, 0.12 mole) was added at once with no exotherm. The mixture was refluxed two hours with the formation of white solids. After cooling, the material was added to cold water to remove by-product triethylamine hydrochloride. The water insoluble material was collected.

Melting point: 294°–300° C.

Elemental analysis Calc.: C, 30.76; H, 5.17; N, 53.82. Found: C, 30.44; H, 5.05; N, 52.13.

EXAMPLE 3

N'-Methyl-N-(Tetrazol-5-yl) Urea

5-Aminotetrazole (5.5 g, 0.065 mole) was dissolved in 75 ml of DMF. On the addition of methylisocyanate (5 g) the temperature began to slowly rise to 40° C. with the formation of a white solid. The solution was heated for 90 minutes at 100° C. and on cooling, poured into cold water. The resulting white solid was filtered, water washed and dried to give 8.3 g of product which softened at 264°–267° C. but was not melted completely at 305° C.

Analysis for $C_3H_6N_6O$: Calc.: C, 25.35; H, 4.25; N, 59.14. Found: C, 25.55; H, 4.20; N, 59.59.

EXAMPLE 4

N-(Tetrazol-5-yl) ethyl carbamate

5-Aminotetrazole (42.5 g, 0.5 mole) was slurried in 700 ml of acetonitrile. On addition of triethylamine (70 ml, 0.5 mole), most of the tetrazole dissolved. Ethylchloroformate (60 ml, 0.61 mole) was slowly added as the mixture exothermed to 65° C. The resulting thick, white slurry was refluxed two hours, cooled and poured into 900 ml of cold water. The insoluble product was filtered off and washed with water and ether. On drying, 71.2 g of product (91 percent) was obtained with a melting point of 259°–263° C. Elemental analysis Calc.: C, 30.58; H, 4.49; N, 44.58. Found: C, 30.33; H, 4.34; N, 44.45.

EXAMPLES 5–8

The decomposition temperatures of the novel blowing agents prepared in EXAMPLES 1–4 were determined by differential scanning colorimetry. The results are recorded in TABLE I below.

Comparative Example A

The decomposition temperature of 5-phenyl tetrazole (Expandex®5PT, a product of Olin Corporation) a commercial blowing agent, was determined by the same procedure as used in EXAMPLES 5–8. The results are given in TABLE I below.

TABLE I

| Example | Compound | Decomposition Temperature C. |
|---|---|---|
| 5 | N—(Tetrazol-5-yl) urea | >315 |
| 6 | N',N'—Dimethyl-N—(tetrazol-5-yl) urea | 295 |
| 7 | N'Methyl-N—(Tetrazol-5-yl) Urea | 264 |
| 8 | N—(Tetrazol-5-yl) ethyl carbamate | 259 |
| Comp. A | 5-Phenyltetrazole | 218 |

EXAMPLES 9–12

The tetrazole compounds (ea 0.25 g) of EXAMPLES 1, 2, 3, and 4 were each separately blended with 4–6 grams of dioctylphthalate and placed in a test tube connected to a gas buret. The test tube was heated in a sand bath until decomposition occurred. The gas yields are given in TABLE II below. Nitrogen compounds in the decomposition gases for EXAMPLES 9 and 12 were identified by gas chromatography.

Comparative Example B

The procedure of EXAMPLES 9–12 was carried out exactly using 5-phenyltetrazole as the blowing agent. The results are give in TABLE II below.

TABLE II

| | Gas Yields and Compositions | | |
| Example | Blowing Agent | Gas Yield (ml/g) | N-containing gases |
| --- | --- | --- | --- |
| 9 | N—(Tetrazol-5-yl) urea | 361 | $N_2$ |
| 10 | N',N'—Dimethyl-N—(tetrazol-5-yl) urea | 215 | — |
| 11 | N'—Methyl-N—(Tetrazol-5-yl) Urea | 183 | — |
| 12 | N—(Tetrazol-5-yl) ethyl carbamate | 191 | $N_2$ |
| Comp. B | 5-Phenyltetrazole | 175 | $N_2$ |

What is claimed is:

1. Tetrazole compounds represented by the formula:

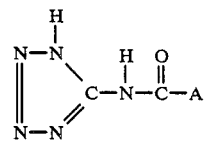

wherein
A represents NRR',
R represents a lower alkyl group, and
R' represents a lower alkyl group.

2. The tetrazole compounds of claim 1 in which R and R' individually represent a lower alkyl group having from 1 to about 6 carbon atoms.

3. The tetrazole compounds of claim 2 in which R and R' individually represent a methyl or ethyl group.

4. The tetrazole compounds of claim 3 in which R and R' represent a methyl group.

* * * * *